(12) United States Patent
Cooper et al.

(10) Patent No.: US 9,507,136 B2
(45) Date of Patent: Nov. 29, 2016

(54) MODE-SWITCHABLE ILLUMINATION SYSTEM FOR A MICROSCOPE

(71) Applicant: GE HEALTHCARE BIO-SCIENCES CORP., Piscataway, NJ (US)

(72) Inventors: Jeremy R. Cooper, Issaquah, WA (US); William M. Dougherty, Issaquah, WA (US); Steven A. Reese, Issaquah, WA (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 0 days.

(21) Appl. No.: 14/356,410

(22) PCT Filed: Nov. 14, 2012

(86) PCT No.: PCT/SE2012/051260
§ 371 (c)(1),
(2) Date: May 6, 2014

(87) PCT Pub. No.: WO2013/074033
PCT Pub. Date: May 23, 2013

(65) Prior Publication Data
US 2014/0320958 A1    Oct. 30, 2014

Related U.S. Application Data

(60) Provisional application No. 61/560,056, filed on Nov. 15, 2011.

(51) Int. Cl.
| | | |
|---|---|---|
| G02B 21/06 | (2006.01) | |
| G02B 17/02 | (2006.01) | |
| G02B 21/00 | (2006.01) | |
| G01N 21/64 | (2006.01) | |
| G02B 21/16 | (2006.01) | |

(52) U.S. Cl.
CPC ............. *G02B 21/06* (2013.01); *G01N 21/645* (2013.01); *G02B 17/023* (2013.01); *G02B 21/002* (2013.01); *G02B 21/16* (2013.01)

(58) Field of Classification Search
CPC .... G02B 21/06; G02B 21/16; G02B 21/002; G02B 17/023; G02B 21/0032; G02B 21/0048; G02B 21/18; G02B 17/004; G02B 17/008; G01N 21/645; G01B 9/04

USPC .............. 359/388, 385, 798–800, 656–661, 359/629–637, 196.1–226.3; 362/575, 362/341–350, 296.09
See application file for complete search history.

(56) References Cited

U.S. PATENT DOCUMENTS

| | | | |
|---|---|---|---|
| 5,861,982 A | 1/1999 | Takahama et al. | |
| 7,573,635 B2 * | 8/2009 | Uhl | G02B 21/0048 359/368 |

(Continued)

FOREIGN PATENT DOCUMENTS

| | | |
|---|---|---|
| WO | WO 2008/009581 | 1/2008 |

OTHER PUBLICATIONS

Supplementary European Search Report for EP Application No. 12850201.0 mailed Jun. 1, 2015 (5 pages).

*Primary Examiner* — Scott J Sugarman
*Assistant Examiner* — Kristina Deherrera
(74) *Attorney, Agent, or Firm* — Sutherland Asbill & Brennan LLP

(57) ABSTRACT

Illumination system for a microscope system capable of being mode-switchable between a first and a second illumination mode, comprising one source of light for providing a collimated beam of light, at least one selector mirror capable of being positioned in at least two positions to redirect the beam of light in two different beam paths, the first beam path being a direct exit beam path wherein the selector mirror redirects the beam of light along an exit beam path to provide a first illumination mode, the second beam path is a mirror loop path comprising two or more mirrors arranged to redirect the beam of light onto the selector mirror such that it is redirected by the selector mirror a second time along the exit beam path, and wherein mirror loop path comprises at least one optical element arranged to optically alter the beam of light to provide the second illumination mode. According to one embodiment, the first illumination mode is Total Internal Reflection (TIRF) and the second illumination mode is Photokinetics (PK) illumination.

6 Claims, 10 Drawing Sheets

(56) References Cited

U.S. PATENT DOCUMENTS

| | | | |
|---|---|---|---|
| 7,715,078 B2* | 5/2010 | Okugawa | 359/212.1 |
| 2002/0048025 A1 | 4/2002 | Takaoka | |
| 2002/0154311 A1 | 10/2002 | Ivarsson | |
| 2003/0058530 A1 | 3/2003 | Kawano | |
| 2004/0246575 A1 | 12/2004 | Tonooka | |
| 2005/0179903 A1 | 8/2005 | Tsuruta et al. | |
| 2006/0028718 A1 | 2/2006 | Seel et al. | |
| 2011/0069382 A1 | 3/2011 | Toomre et al. | |

* cited by examiner

MODE-SWITCHABLE ILLUMINATION SYSTEM FOR A MICROSCOPE

CROSS-REFERENCE TO RELATED APPLICATIONS

This application is a filing under 35 U.S.C. 371 of international application number PCT/SE2012/051260, filed Nov. 14, 2012, published on May 23, 2013 as WO 2013/074033, which claims priority to application No. 61/560,056 filed Nov. 15, 2011.

FIELD OF THE INVENTION

The present invention relates to a mode-switchable illumination system for a microscope system, and more particularly to an illumination system that is mode-switchable e.g. between Total Internal Reflection Fluorescence (TIRF) and Photokinetics (PK) illumination modes.

BACKGROUND OF THE INVENTION

Total Internal Reflection Fluorescence (TIRF) illumination and photokinetics (PK) illumination are two laser-based modes of illumination that are commonly used in microscopy. A typical TIRF system involves a focused laser beam near the extreme edge of the back focal plane (BFP) of a high numerical aperture (NA) objective lens. This arrangement results in a collimated beam of light that impinges upon the coverslip/sample interface at a steep angle of incidence. If the angle of incidence is steep enough, the light will be totally internally reflected at the coverslip (glass) to sample (water) interface. In this way, only the fluorescent particles that are located proximal (<100 nm) to the coverslip/sample interface are illuminated, thus greatly improving image contrast. Scanning TIRF is an advanced form of TIRF illumination in which the beam is scanned in a circular pattern around the edge of the objective BFP. This technique provides the thin illumination section of conventional TIRF, but greatly reduces many of the artifacts that plague TIRF microscopy including shadowing, scattering, and interference patterns. Additionally, scanning the excitation beam around the back focal plane reduces or eliminates these same artifacts in a conventional laser epifluorescent (non-TIRF) illumination scheme.

In contrast, PK illumination involves a collimated beam of light entering the objective lens so that the beam is brought to a tight focus at the sample plane. This focused beam can be used to cause a number of reactions at precise locations in the sample including but not limited to photoactivation, photobleaching, chemical uncaging, and laser ablation. Scanning PK provides the ability to steer the focused beam to any location within the sample plane without moving the sample itself.

It is desirable to provide both scanning TIRF and PK modes of illumination on a single instrument from a single laser launch point. Furthermore, many experiments can benefit from the ability to rapidly switch between these two modes.

SUMMARY OF THE INVENTION

The object of the invention is to provide a new illumination system for a microscope system capable of being mode-switchable between a first and a second illumination mode, which illumination system overcomes one or more drawbacks of the prior art. This is achieved by the illumination system as defined in the independent claim.

According to one aspect there is provided an illumination system for a microscope system capable of being mode-switchable between a first and a second illumination mode, comprising one source of light for providing a collimated beam of light, at least one selector mirror capable of being positioned in at least two positions to redirect the beam of light in two different beam paths, the first beam path being a direct exit beam path wherein the selector mirror redirects the beam of light along an exit beam path to provide a first illumination mode, the second beam path is a mirror loop path comprising two or more mirrors arranged to redirect the beam of light onto the selector mirror such that it is redirected by the selector mirror a second time along the exit beam path, and wherein mirror loop path comprises at least one optical element arranged to optically alter the beam of light to provide the second illumination mode.

According to one aspect, the mirror loop path comprises an extended mirror loop to provide a predetermined beam path length with respect to the optical element.

According to one aspect, a scan mirror is arranged at the exit beam path to provide selective scanning of an output beam of light.

According to one aspect, scan mirror is arranged to provide selective scanning in 2 dimensions.

According to one aspect, the selector mirror is arranged to provide selective scanning of the beam of light in a first dimension, the scan mirror is arranged to provide selective scanning in a second dimension essentially transverse to the first, and the mutual scanning of the scan mirror and the selector mirror is controlled to provide 2-dimensional scanning of the output beam of light.

According to one aspect, there is provided a second mirror loop path selectively addressed by the scan mirror and comprising two or more mirrors arranged to redirect the beam of light onto the scan mirror such that it is redirected by the scan mirror a second time along the exit beam path, whereby the exit beam is scanned by a parallel translation.

According to one aspect, there is provided at least one exit optical element which is optically matched and positioned with respect to the at least one optical element in the mirror loop path, and arranged to optically alter the beam of light to provide the first and second illumination modes.

The exit optical element may be an exit lens arranged to focus the beam of light at the back aperture of an objective of a microscope system, and wherein the optical element in the mirror loop path is a lens arranged to focus the beam of light at a predetermined point along the beam path before the beam of light reaches the exit lens whereby the thus converging beam of light is re-collimated.

According to one aspect, the first illumination mode is Total Internal Reflection (TIRF) and the second illumination mode is Photokinetics (PK) illumination.

There is further provided a microscope system comprising an illumination system capable of being mode-switchable between a first and a second illumination mode.

The general solution presented here is, according to one embodiment, to use a tilt mirror (preferably but not limited to a galvo-mirror) both to direct the beam down separate paths and to redirect the beams from those two separate paths along a common exit path toward the objective lens. This approach requires that for at least one of the two modes, the beam must reflect off of the tilt mirror two or more times (once to direct it down the alternate path and once to redirect it along the common exit path). By adding a second tilt mirror or replacing it with a dual-axis tip/tilt mirror, this arrangement can provide full scanning capability of the focused beam around the entire back focal plane (in TIRF mode) or around the entire sample plane (in PK mode). It also provides the ability to scan the beam in a conventional epifluorescent (non-TIRF) manner by slightly reducing the amplitude of the scan angle. In this manner, the diameter of the circle that the beam scribes at the objective back aperture is smaller than the threshold necessary to generate total internal reflection at the sample interface. Furthermore, the system provides the ability to generate very steep (near TIRF) transmission angles through the sample, thereby greatly improving image contrast by reducing the excitation of fluorophores that lie above or below the sample focus plane.

The approach described here overcomes many of the shortcomings of previous approaches by performing both the path bifurcation and path rejoining on the same optical device. This serves to both reduce the complexity and cost of the system while improving efficiency. Furthermore, this system does not require multiple laser launch points or expensive and complicated beam recombination optical components or polarizers. Lastly, it is easily amenable to providing full scanning of the beam in TIRF, conventional epifluorescent, or PK modes and switching between modes can be accomplished very fast, on the order of 2 ms.

A more complete understanding of the present invention, as well as further features and advantages thereof, will be obtained by reference to the following detailed description and drawings.

DETAILED DESCRIPTION OF THE INVENTION

Figure 1:
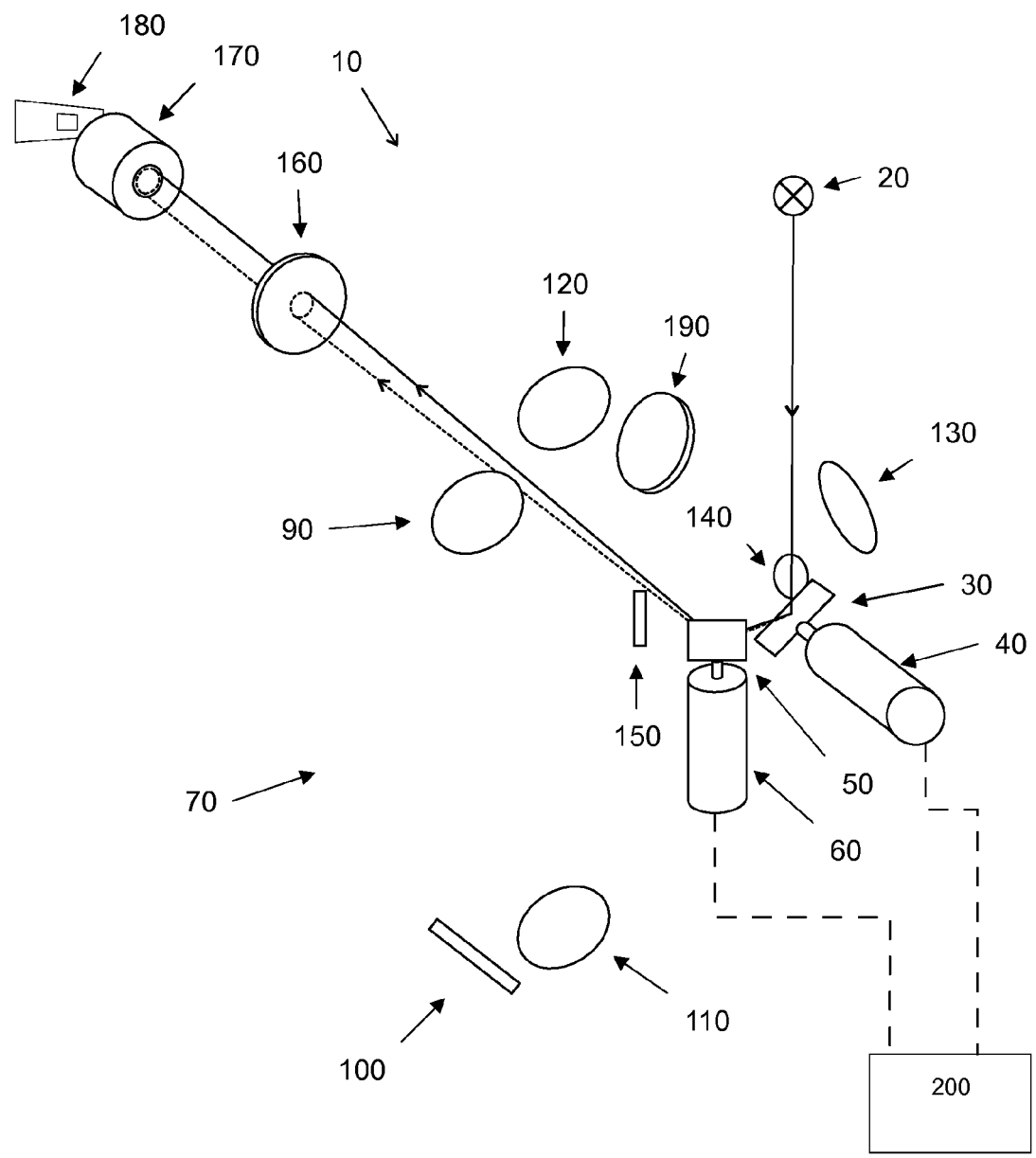
FIGS. 1 and 2 show a schematic representation of an example of an illumination system for a microscope system capable of being mode-switchable between a first and a second illumination mode according to one embodiment of the present invention.
Figure 2:
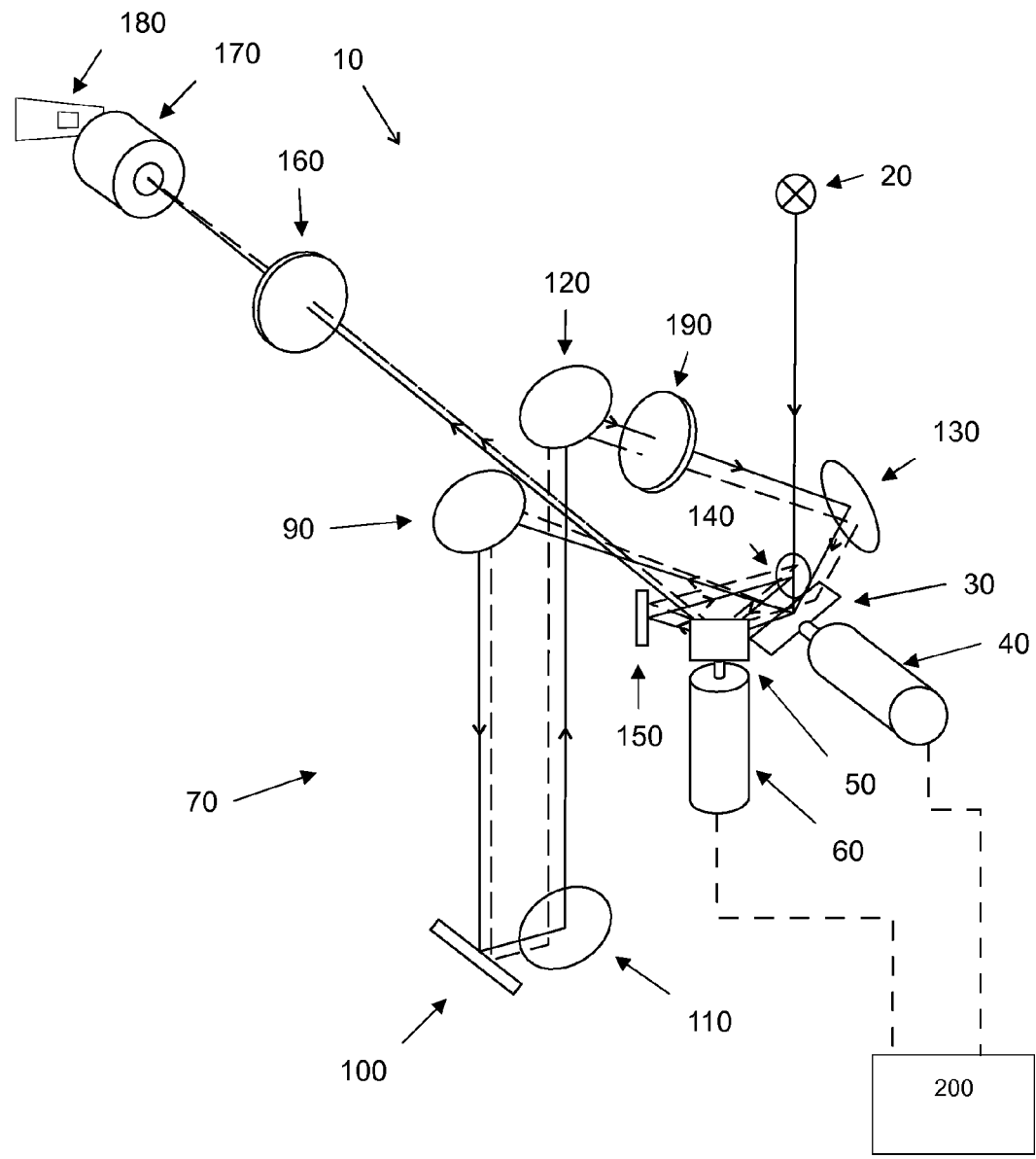

FIGS. 1 and 2 show a schematic representation of an example of an illumination system for a microscope system capable of being mode-switchable between a first and a second illumination mode according to one embodiment of the present invention. In the disclosed embodiment, the illumination system the first illumination mode is Total Internal Reflection (TIRF) and the second illumination mode is Photokinetics (PK) illumination. FIG. 1 shows the illumination system in TIRF mode, whereas FIG. 2 shows the illumination system in PK mode. The system comprises a source of illumination 20, e.g. a laser source, arranged to provide a collimated beam of light 22. A first scanning mirror 30 (also referred to as selector mirror in some embodiments) driven for scanning rotation about a first axis by a drive unit 40, e.g. a galvo driver, a piezo driver or the like. In FIG. 1 the first scanning mirror is positioned in a first general direction to reflect the beam of light onto a second scanning mirror 50 driven for scanning rotation about a second axis of rotation, preferably transverse to the first, by a drive unit 60. In FIG. 1 the second scanning mirror 50 is arranged in a first general position to redirect the beam of light along an exit beam path 52 whereby it passes through lens 160 arranged to focus the light beam at the back aperture of objective 170. A control unit 200 is connected to and arranged to control the scan position of the first and second scanning mirrors 30 and 50. In the illumination mode of FIG. 1, the first and second scanning mirrors 30 and 50 are arranged to be scanned within their respective first general positions to thereby selectively position the exit beam of light at the, e.g. for scanning TIRF, desired positions at the edge of the back focal plane of the objective 170 as indicated by the dotted circle in FIG. 1. In FIG. 1, the scanning TIRF mode is illustrated by two beam paths (solid and dotted) extending from the first scanning mirror 30 to the back aperture of the objective 170. However it should be noted that the disclosed embodiment is arranged to scan one beam of light and that each one of the disclosed beam path represents a two different mutual positions of the first and second scanning mirrors 30 and 50 respectively.

In FIG. 2, the system is shown in Photokinetics Illumination mode, wherein both first and second scanning mirrors 30 and 50 are arranged in a second general position, respectively. When arranged in said second general position, scanning mirror 30 redirects the beam of light into a first mirror loop 70 comprising mirrors 90, 100, 110, 120 and 130 arranged to redirect the beam of light onto the first scanning mirror 30 a second time. Thereafter the beam of light is directed onto the second scanning mirror 50. In its second general position, the second scanning mirror 50 is arranged to redirect the beam of light into a second mirror loop comprised of mirrors 140 and 150 which are arranged to redirect the beam of light onto the second scanning mirror 50 a second time.

As previously is mentioned, the Photokinetics Illumination mode involves scanning the angle of a collimated beam of light at the back aperture of the objective 170. This results in scanning the position of the focused spot in the sample plane. In the disclosed system, this is accomplished by the incorporation of a lens 190 in the first mirror loop 70 arranged to focus the beam of light at a predetermined point along the beam path before the beam of light reaches lens 160 whereby the thus converging beam of light is re-collimated. The angle of the light beam at the back focal plane of the objective 170 may be scanned as the first and second scanning mirrors 30 and 50 are arranged to be scanned within their respective second general positions to thereby selectively position the exit beam of light.

As is explained in greater detail with reference to FIGS. 3-5 below, the first and second mirror loop arrangements may be designed to achieve a pure translation of the light beam. In the first mirror loop comprising the lens 190 this is accomplished by means of an uneven number reflections of mirrors in the loop, and it should be noted that the disclosed embodiment using 5 static mirrors 90, 100, 110, 120 and 130 in the loop should not be considered limiting but merely serve as an example of how such a loop may be designed. As will be disclosed below, e.g. in FIGS. 6 and 7, the first mirror loop may be designed using only two mirrors. In the embodiment of FIGS. 1 and 2, the positioning of individual mirrors and other components represents one design wherein the optical path-lengths between different components have been taken into consideration in order to provide an functional and space effective illumination system. In particular, the mirrors 100, 110 and 120 are included in the design to establish an elongated path-length between the first scanning mirror 30 and the lens 190, as is further disclosed in FIG. 8. In the second mirror loop the pure translation is achieved by 2 mirrors, but additional mirrors may be included also in the second loop to provide an elongated path-length if desired.

In case a pure mode selection unit is sufficient, the second scanning mirror may be omitted and the first scanning mirror may only have to be positioned in two fixed positions corresponding to the above general positions.

By these embodiments, the first scanning mirror is used both to direct the beam down separate paths and to redirect the beams from those two separate paths along a common exit path toward the objective lens.

In one embodiment, not shown, there may even be two or more mirror loops associated with one scanning mirror whereby alternative optical components may be introduced in the light path. In one embodiment, the optical elements, e.g. lenses 160 and 190, may be replaced by one or more other optical element, such as a filter or other optical elements arranged to optically alter the beam of light, or they may be placed at different positions in the light path where they are included or excluded from the light path as controlled by switching the mirror loops in and out.

Figure 3A:
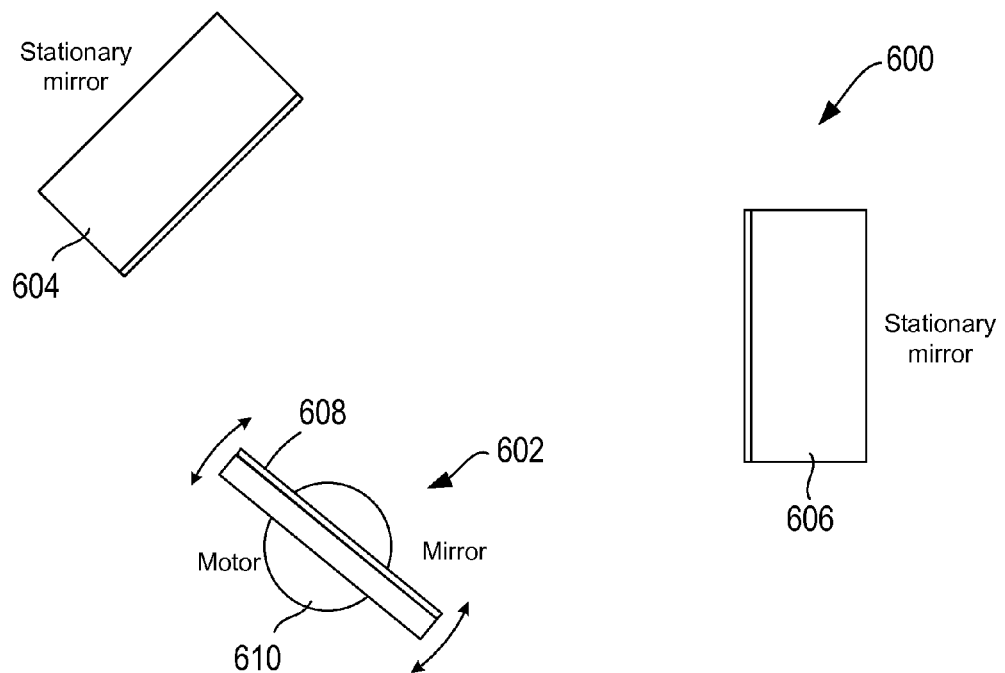
FIGS. 3A-3B show a top-plan view and an isometric view of an example beam translator.
Figure 3B:
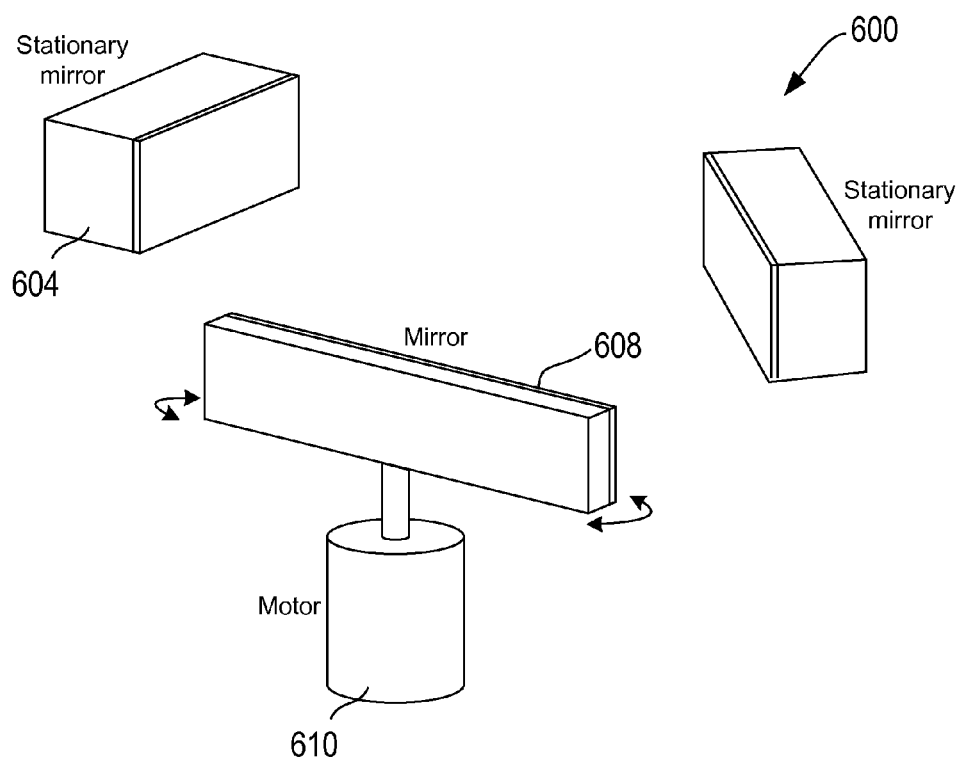

FIGS. 3A-3B show a top-plan view and an isometric view of an example beam translator 600 comprising a mirror loop as disclosed in the previous embodiments. The translator 600 includes a scanning mirror 602, a first flat stationary mirror 604 and a second flat stationary mirror 606. The reflective surface of the stationary mirror 604 is angled toward the region between the scanning mirror 602 and stationary mirror 606, and the reflective surface of the stationary mirror 606 is angled toward the region between the scanning mirror 602 and the stationary mirror 604. In the example of FIGS. 3A-3B, the scanning mirror 602 is a galvanometer mirror that includes a flat pivot mirror 608 attached to a rotatable shaft of a motor 610, which can be a galvanometer motor or a stepper motor. Alternatively, the scanning mirror can be a piezoelectric controlled mirror. As shown in FIGS. 3A-3B, the mirror 608 is continuously rotated back and forth by the motor 610 through a range of angles.

Figure 4:
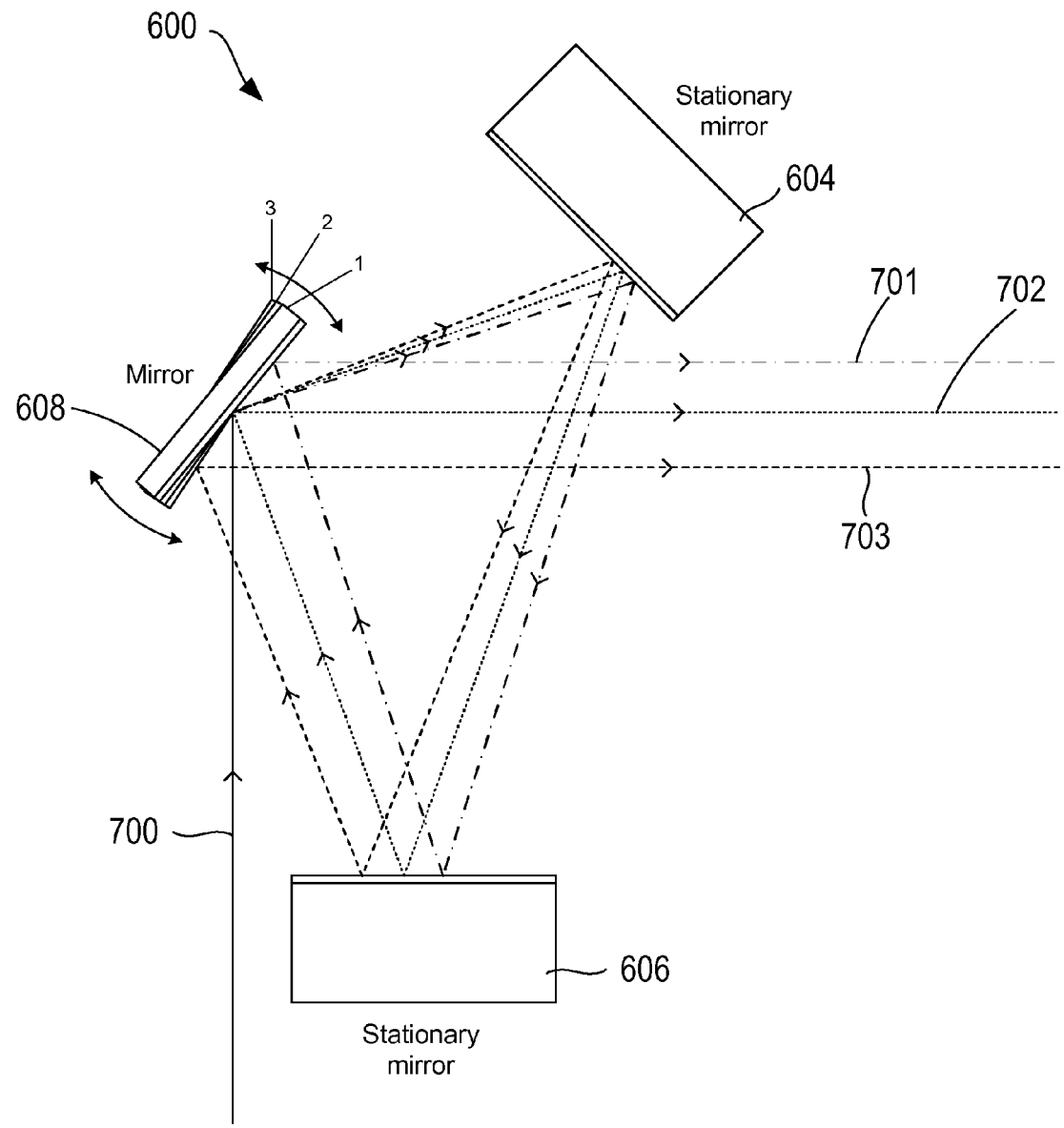
FIG. 4 shows as example demonstration of the beam translator shown in FIG. 3.

FIG. 4 shows a top-plan view of the beam translator 600 in operation. A beam of light 700, such as a beam of light output from the light source 102 as described above, is directed toward the mirror 608. FIG. 4 shows the mirror 608 rotated in three positions 1, 2 and 3, which represent just three of a continuum of rotational positions for the mirror 608. Differently patterned lines 701-703 represent three different paths the beam 700 travels through the translator 600 when the pivot mirror 608 is rotated into one of the three positions 1, 2 and 3, respectively. As shown in the example of FIG. 4, the stationary mirrors 604 and 606 and the pivot mirror 608 are positioned so that the beam is output along one of three substantially parallel paths via four reflections. In other words, the mirror 608 can be rotated into any of one of a continuum of positions that result in the beam being output from the translator 600 after four reflections along one of a continuum of substantially parallel paths. Ideally the output paths along which the output beam can travel are parallel or non-intersecting, but in practice, it is recognized that the paths may be only approximately parallel or intersect at very long distances away from the translator 600 due to slight variations in the relative placement and orientation of the mirrors. As a result, the paths along which the beam can be output from the translator 600 are referred to as approximately parallel.

For each rotational position of the pivot mirror 608 that results in the beam 700 being placed on one of the parallel paths, the beam 700 is reflected off of the pivot mirror 608 two times, the stationary mirror 604 one time, and the stationary mirror 606 one time for a total of four reflections. FIGS. 5A-5C show snapshots of internal paths the beam 700 traveling through the translator 600 when the pivot mirror 608 is rotated into the three positions 1, 2 and 3, respectively. In FIG. 5A, the pivot mirror 608 is rotated into position 1. The beam 700 strikes the pivot mirror 608 at the point 802 and undergoes four reflections off of the mirrors 604, 606 and 608 with the reflections numbered sequentially 1, 2, 3 and 4. The $4^{th}$ reflection off of the pivot mirror 608 at the point 804 places the beam on the path 701 also shown in FIG. 8. In FIG. 5B, the pivot mirror 608 is rotated into position 2. The beam 700 strikes the pivot mirror 608 at the point 806 and undergoes four reflections off of the mirrors 604, 606 and 608 with the reflections numbered sequentially 1', 2', 3' and 4'. The $4'^{th}$ reflection off of the pivot mirror 608 near the point 806 places the beam on the path 702 also shown in FIG. 8. In FIG. 5C, the pivot mirror or 608 is rotated into position 3. The beam 700 strikes the pivot mirror 608 at the point 808 and undergoes four reflections off of the mirrors 604, 606 and 608 with the reflections numbered sequentially 1", 2", 3" and 4". The $4''^{th}$ reflection off of the pivot mirror 608 at the point 810 places the beam on the path 703 also shown in FIG. 8.

When the beam translator 600 is implemented with a galvanometer mirror for the scanning mirror 602 sub-millisecond translation of the output beam is attainable.

Figure 5:
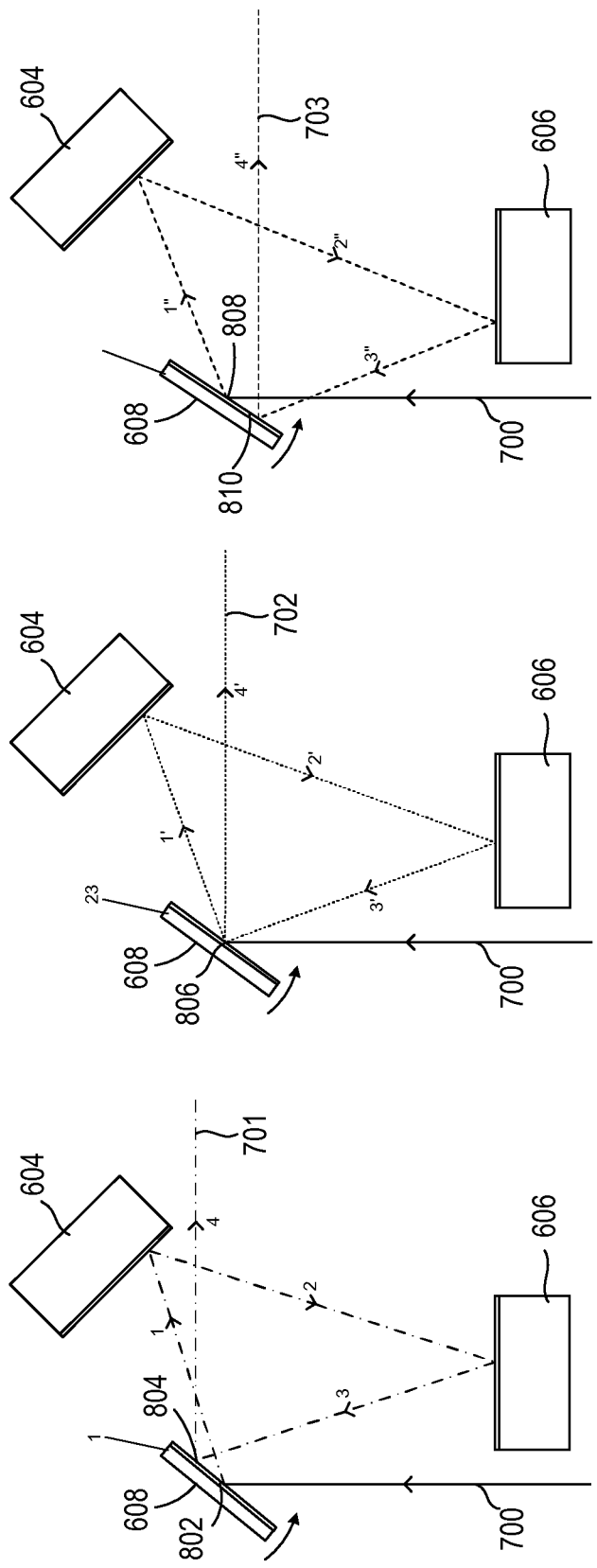
FIGS. 5A-5C show snapshots of internal paths associated with a beam of light traveling through the beam translator shown in FIG. 3.
Figure 6:
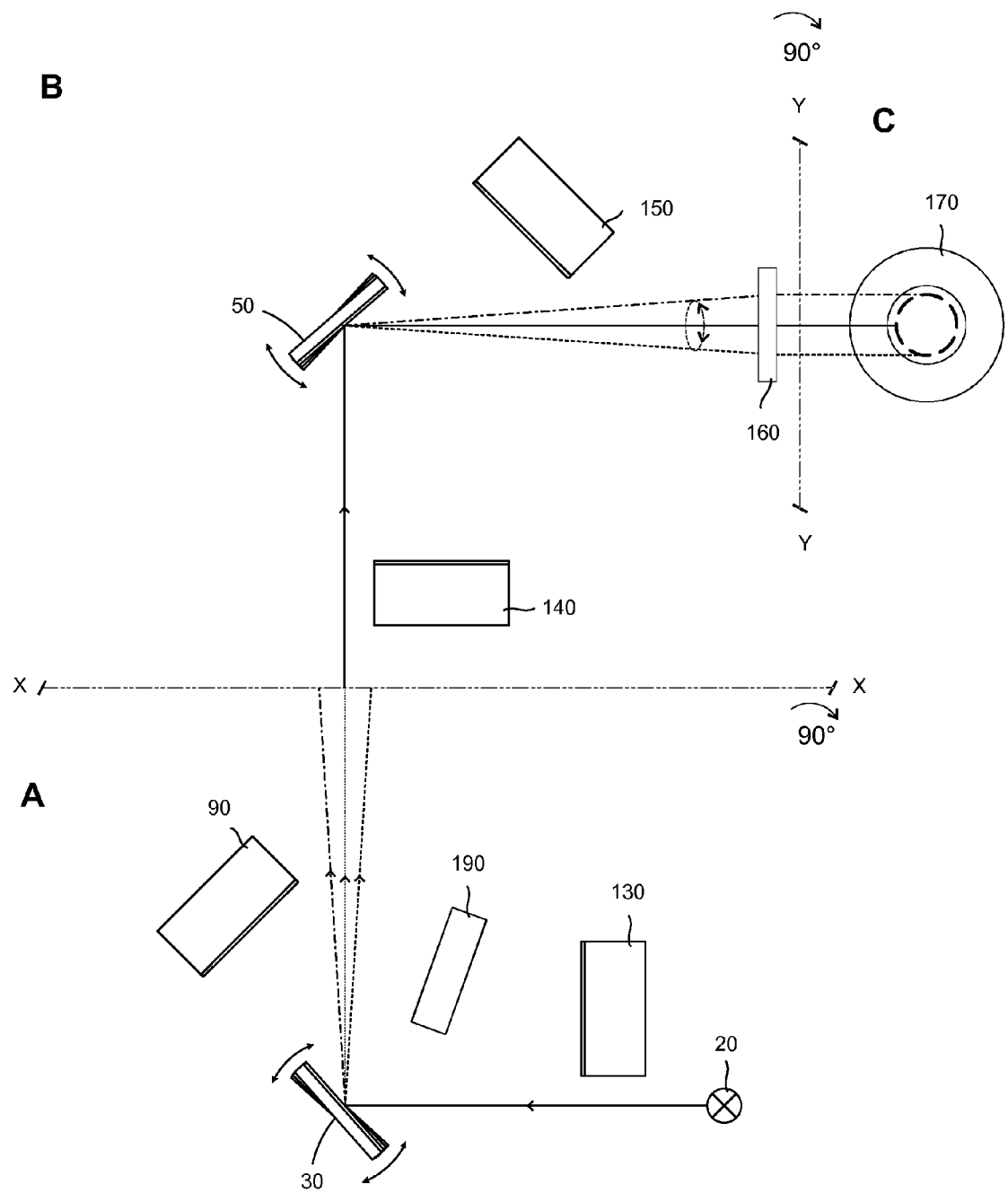
FIGS. 6-8 show simplified representations of the illumination system of FIGS. 1-2.
Figure 7:
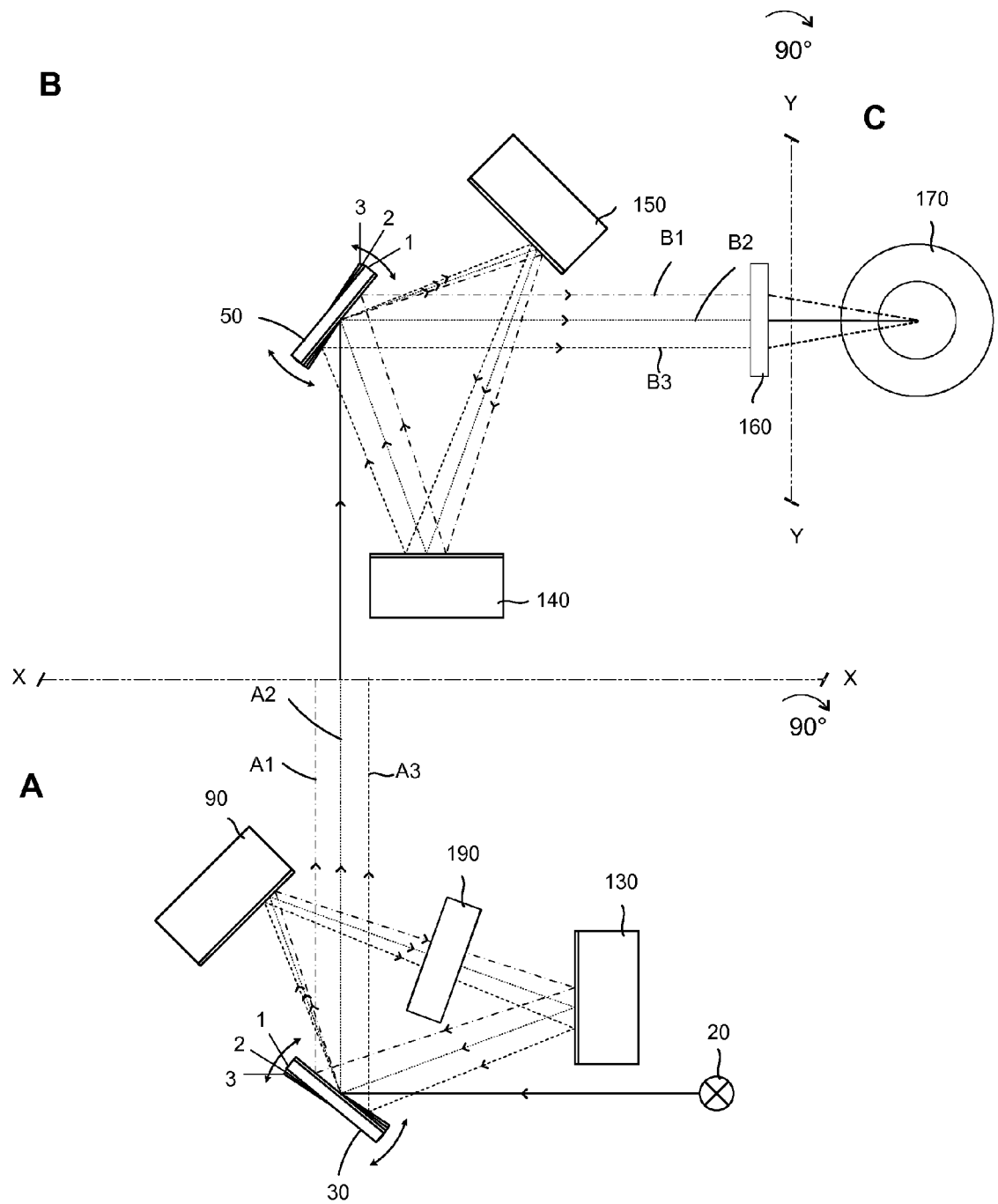
Figure 8:
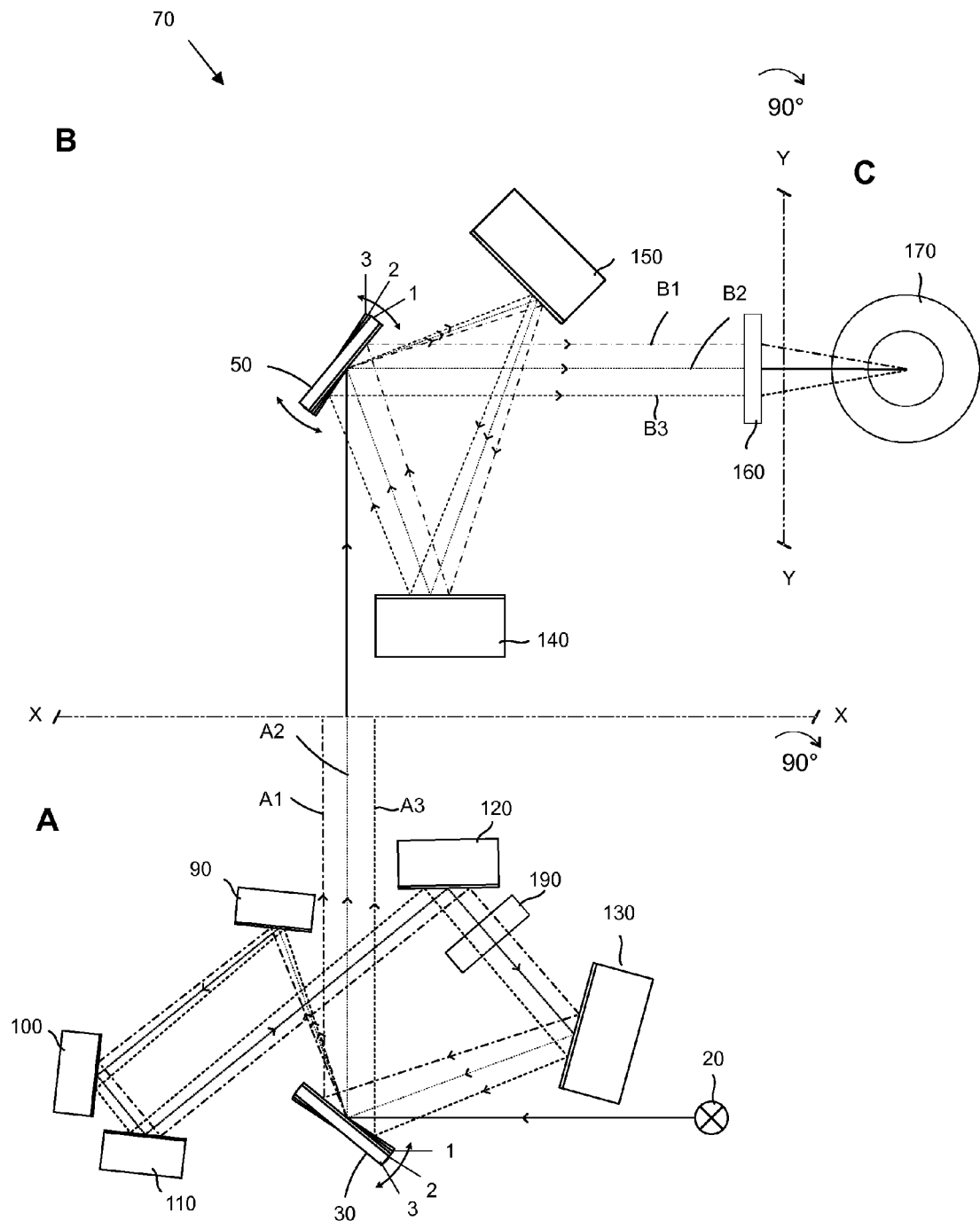

FIGS. 6 and 7 shows a general representation of the illumination system of FIGS. 1 and 2, but wherein the 3-dimensional representation of the system and the beam path has been transformed into a simplified 2 dimensional figure based on the beam translator 600 of FIG. 3-5. In FIGS. 6 and 7 the first and second scanning mirrors 30 and 50 and their associated mirrors have been separated into two schematic beam translator sections, A and B respectively. In order to provide a simplified representation of the illumination system, the beam translator of section A is shown rotated by approximately 90° with respect to the beam translator of section B. It should be noted that the angle of rotation of the two sections A and B with respect to each other need not to be exactly 90°, but that it is sufficient that the rotation is large enough to achieve the desired scanning capability of the output beam of light from the system. In FIGS. 6 and 7 the first scan/selector mirror 30 of section A is arranged to scan the beam of light in a first dimension, i.e. a first scan plane, and the second scan mirror 50 of section B is arranged to scan the beam of light in a second dimension, second scan plane, which is essentially orthogonal to the first dimension. Thus, by selectively controlling the mutual scanning of the first scan/selector mirror 30 and the second scan mirror 50 2-dimensional scanning of the output beam of light is provided. Further, in FIGS. 6 and 7 also the back end of the objective 170 is shown rotated by 90° with respect to the beam translator of section B in order to better display the output beam of light from the illumination system. As briefly mentioned above, in FIGS. 6 and 7, mirrors 100, 110 and 120 of FIGS. 1 and 2 are omitted in order to more clearly show the basic principles of the switching between a first and a second illumination mode using beam translator sections A and B. However, FIG. 8 shows a corresponding simplified representation of an illumination system comprising said mirrors to provide an elongated or otherwise reconfigured optical path.

As is mentioned above, in the embodiment of FIGS. 1-2 and 6-7, both beam translator sections A and B respectively are arranged to provide essentially parallel translation of the beam of light.

Figure 9:
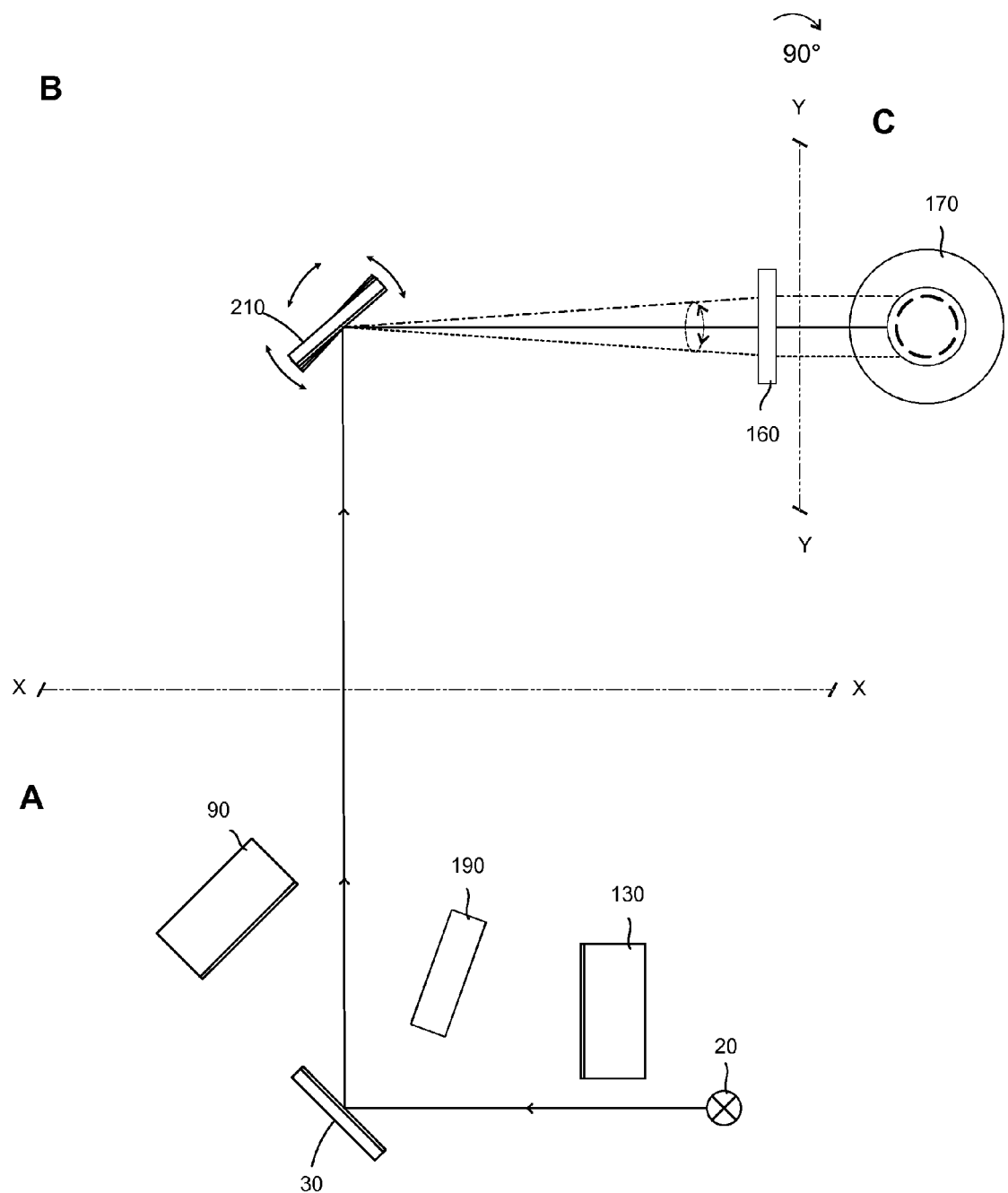
FIGS. 9 and 10 show a simplified representations of an alternative embodiment of a mode-switchable illumination system of FIGS. 1-2
Figure 10:
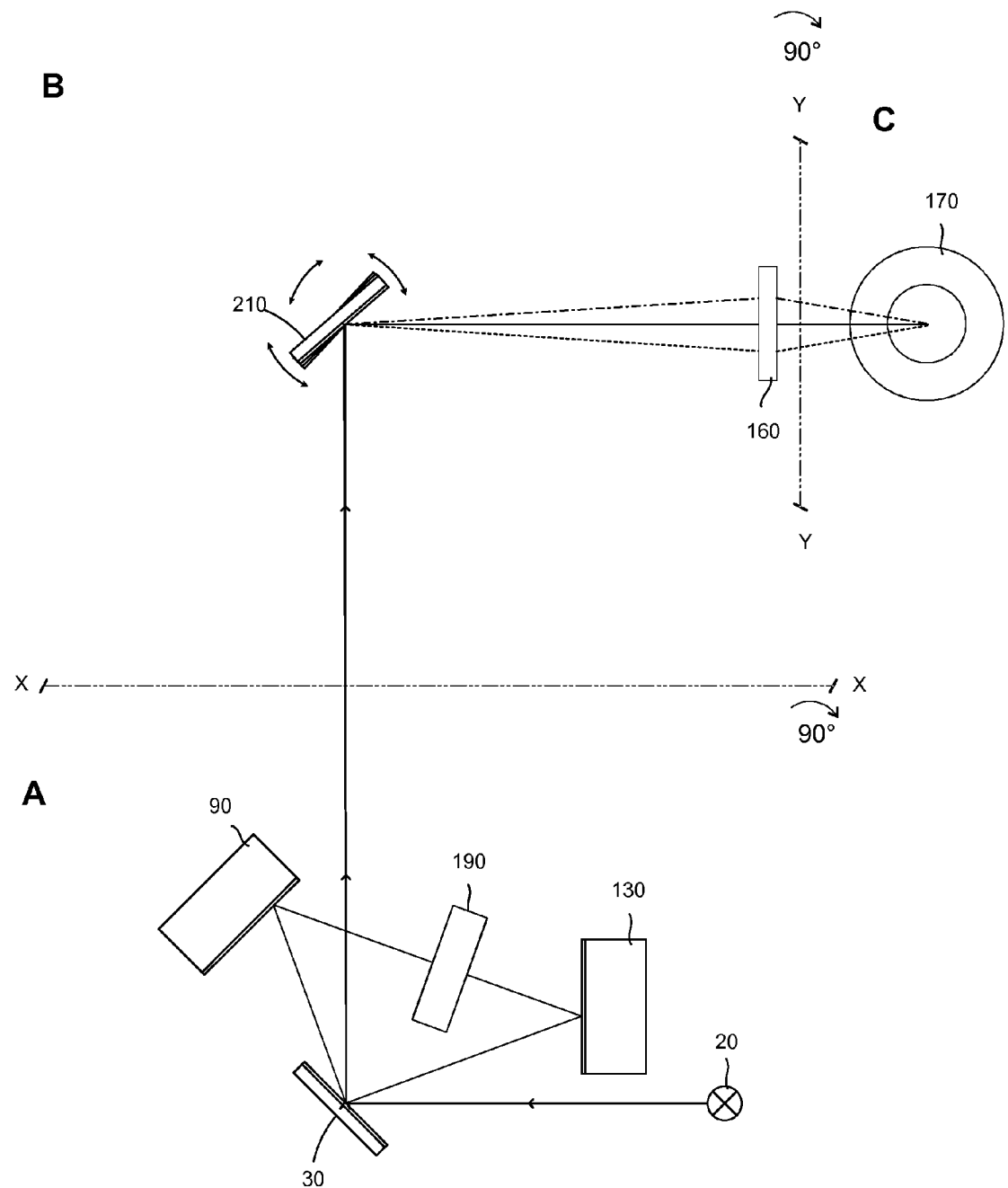

According to one embodiment, schematically disclosed in FIGS. 9 and 10, the beam translator section A may be used as a pure mode switch for selectively switching one or more optical elements into and out of the optical beam path of an illumination system. In the disclosed embodiment, the scan mirror 50 of previous embodiments is replaced by a scan mirror 210 capable of scanning in 2 dimensions in order to provide the desired scanning of the output light beam.

The illumination system capable of being mode-switchable between a first and a second illumination mode according to the present invention may e.g. be provided as a modular add on unit for a suitable microscope system, or it may be integrated as an integral part of a microscope, and it should be noted that the illumination system need not to be limited to switching between two illumination modes, but it may provide a broad ranges of illumination modes as well as suitable intermediate illumination modes.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. They are not intended to be exhaustive of or to limit this disclosure to the precise forms described. Obviously, many modifications and variations are possible in view of the above teachings. The examples are shown and described in order to best explain the principles of this disclosure and practical applications, to thereby enable others skilled in the art to best utilize this disclosure and various examples with various modifications as are suited to the particular use contemplated. It is intended that the scope of this disclosure be defined by the following claims and their equivalents.

What is claimed is:

1. An illumination system for a microscope system capable of being mode-switchable between a first and a second illumination mode comprising:
   one source of light for providing a collimated beam of light;
   at least one selector mirror capable of being positioned in at least two positions to redirect the beam of light in two different beam paths,
      the first beam path being a direct exit beam path wherein the selector mirror redirects the beam of light along an exit beam path to provide a first illumination mode,
      the second beam path being a mirror loop path comprising two or more mirrors wherein the selector mirror redirects the beam of light along the exit beam path after first redirecting the beam of light to one of the two or more mirrors and after one of the two or more mirrors redirects the beam of light back to the selector mirror,
   wherein the first mirror loop path comprises at least one optical element arranged to optically alter the beam of light to provide the second illumination mode, and
   wherein the selector mirror is arranged to provide selective scanning of the beam of light in a first dimension; and
   a scan mirror arranged at the exit beam path to provide selective scanning of an output beam of light, and
   wherein the illumination system further comprises a second mirror loop path selectively addressed by the scan mirror and comprising two or more mirrors arranged to redirect the beam of light onto the scan mirror such that it is redirected by the scan mirror a second time along the exit beam path, whereby the exit beam is scanned by a parallel translation, and
   wherein the scan mirror is arranged to provide selective scanning in a second dimension essentially transverse to the first dimension, and the mutual scanning of the scan mirror and the selector mirror is controlled to provide 2-dimensional scanning of the output beam of light.

2. An illumination system of claim 1, wherein the first mirror loop path comprises an extended mirror loop to provide a predetermined beam path length with respect to the optical element.

3. An illumination system of claim 1, comprising at least one exit optical element which is optically matched and positioned with respect to the at least one optical element in the first mirror loop path, and arranged to optically alter the beam of light to provide the first and second illumination modes.

4. An illumination system of claim 3, wherein the exit optical element is an exit lens arranged to focus the beam of light at the back aperture of an objective of a microscope system, and wherein the optical element in the first mirror loop path is a lens arranged to focus the beam of light at a predetermined point along the beam path before the beam of light reaches the exit lens whereby the beam of light is re-collimated.

5. An illumination system of claim 1, wherein the first illumination mode is Total Internal Reflection (TIRF) and the second illumination mode is Photokinetics (PK) illumination.

6. A microscope system comprising the illumination system of claim 1.

* * * * *